(12) United States Patent
Hager et al.

(10) Patent No.: US 9,056,188 B2
(45) Date of Patent: Jun. 16, 2015

(54) NEEDLE SHIELDING FLAG STRUCTURES

(75) Inventors: Jörgen Bruno Hager, Helsingborg (SE); Johan Fredrik Thörne, Helsingborg (SE); Bengt Erik Anders Nilsson, Helsingborg (SE)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 11/943,351

(22) Filed: Nov. 20, 2007

(65) Prior Publication Data

US 2008/0140011 A1 Jun. 12, 2008

Related U.S. Application Data

(60) Provisional application No. 60/867,047, filed on Nov. 22, 2006.

(51) Int. Cl.
*A61M 25/06* (2006.01)
*A61M 5/32* (2006.01)

(52) U.S. Cl.
CPC .......... *A61M 25/0606* (2013.01); *A61M 5/3275* (2013.01); *A61M 25/0625* (2013.01); *A61M 25/0637* (2013.01); *A61M 2005/325* (2013.01)

(58) Field of Classification Search
CPC .......... A61M 5/3275; A61M 25/0606; A61M 25/0625; A61M 25/0637; A61M 2005/325
USPC .............. 604/110, 162, 163, 164.01, 164.08, 604/192, 198, 263, 264
See application file for complete search history.

(56) References Cited

U.S. PATENT DOCUMENTS

| | | | |
|---|---|---|---|
| 4,929,241 A | 5/1990 | Kulli | |
| 4,952,207 A | 8/1990 | Lemieux | |
| 4,970,998 A * | 11/1990 | Tyler | 123/185.3 |
| 4,978,344 A | 12/1990 | Dombrowski et al. | |
| 5,051,109 A | 9/1991 | Simon | |
| 5,053,017 A | 10/1991 | Chamuel | |
| 5,135,504 A | 8/1992 | McLees | |
| 5,215,528 A | 6/1993 | Purdy et al. | |
| 5,279,591 A | 1/1994 | Simon | |
| 5,322,517 A | 6/1994 | Sircom et al. | |
| 5,328,482 A | 7/1994 | Sircom et al. | |
| 5,419,766 A | 5/1995 | Chang et al. | |
| 5,458,658 A | 10/1995 | Sircom | |
| 5,533,974 A | 7/1996 | Gaba | |
| 5,562,633 A | 10/1996 | Wozencroft | |

(Continued)

FOREIGN PATENT DOCUMENTS

WO   WO 2004/065713 A1   8/2004
WO   2005/079891 A1   9/2005

*Primary Examiner* — Nathan R Price
(74) *Attorney, Agent, or Firm* — Jeanne Lukasavage; Craig Metcalf; Kirton McConkie

(57) ABSTRACT

An extravascular system for accessing the vasculature of a patient may include a catheter, a needle disposed within the catheter, and/or a needle tip shield assembly. The needle tip shield assembly may have a needle cap, the needle cap may have a needle shield, and the needle shield may have one or more flags. The flags may include a first flag and a second flag. The first flag and the second flag may form an engageable barrier through which the needle cannot penetrate once the barrier is engaged. The needle shield may be a V-clip. The V-clip may include a first arm and a second arm, and the first flag may be secured to the first arm while the second flag may be secured to the second arm.

18 Claims, 6 Drawing Sheets

(56) References Cited

U.S. PATENT DOCUMENTS

| | | |
|---|---|---|
| 5,662,610 A | 9/1997 | Sircom |
| 5,697,907 A | 12/1997 | Gaba |
| 5,718,688 A | 2/1998 | Wozencroft |
| 5,823,997 A | 10/1998 | Thorne |
| 5,853,393 A | 12/1998 | Bogert |
| 5,951,515 A | 9/1999 | Osterlind |
| 6,056,726 A | 5/2000 | Isaacson |
| 6,117,108 A | 9/2000 | Woehr et al. |
| 6,234,999 B1 | 5/2001 | Wemmert et al. |
| 6,287,278 B1 | 9/2001 | Woehr et al. |
| 6,322,537 B1 | 11/2001 | Chang |
| 6,443,929 B1 | 9/2002 | Kuracina et al. |
| 6,616,630 B1 | 9/2003 | Woehr et al. |
| 6,620,136 B1 | 9/2003 | Pressly, Sr. et al. |
| 6,629,959 B2 | 10/2003 | Kuracina et al. |
| 6,641,555 B1 | 11/2003 | Botich et al. |
| 6,652,486 B2 | 11/2003 | Bialecki et al. |
| 6,692,471 B2 | 2/2004 | Boudreaux |
| 6,702,595 B2 | 3/2004 | Nelson et al. |
| 6,709,419 B2 | 3/2004 | Woehr |
| 6,749,588 B1 | 6/2004 | Howell et al. |
| 6,860,871 B2 | 3/2005 | Kuracina et al. |
| 6,981,965 B2 | 1/2006 | Luther et al. |
| 7,018,344 B2 | 3/2006 | Bressler et al. |
| 7,097,633 B2 | 8/2006 | Botich et al. |
| 7,160,269 B2 | 1/2007 | Woehr |
| 7,186,239 B2 | 3/2007 | Woehr |
| 7,201,740 B2 | 4/2007 | Crawford |
| 7,214,211 B2 | 5/2007 | Woehr et al. |
| 7,226,434 B2 | 6/2007 | Carlyon et al. |
| 7,238,169 B2 | 7/2007 | Takagi et al. |
| 7,264,613 B2 | 9/2007 | Woehr et al. |
| 2002/0169418 A1 | 11/2002 | Menzi et al. |
| 2003/0114797 A1 | 6/2003 | Vaillancourt et al. |
| 2003/0144627 A1 | 7/2003 | Woehr et al. |
| 2003/0167062 A1 | 9/2003 | Gambale et al. |
| 2003/0199827 A1 | 10/2003 | Thorne |
| 2003/0228808 A1 | 12/2003 | Nelson et al. |
| 2004/0010227 A1 | 1/2004 | Riesenberger et al. |
| 2004/0049155 A1 | 3/2004 | Schramm |
| 2004/0162525 A1 | 8/2004 | Vaillancourt et al. |
| 2004/0225260 A1 | 11/2004 | Villa et al. |
| 2004/0243061 A1 | 12/2004 | McGurk |
| 2005/0027263 A1 | 2/2005 | Woehr et al. |
| 2005/0070855 A1 | 3/2005 | Ferguson et al. |
| 2005/0080378 A1 | 4/2005 | Cindrich et al. |
| 2005/0182362 A1 | 8/2005 | Sircom et al. |
| 2006/0074384 A1 | 4/2006 | Kohler |
| 2006/0116638 A1 | 6/2006 | Woehr et al. |
| 2006/0270980 A1 | 11/2006 | Menzi et al. |
| 2007/0038179 A1 | 2/2007 | Bialecki et al. |
| 2007/0038182 A1 | 2/2007 | Bialecki et al. |
| 2007/0038183 A1 | 2/2007 | Bialecki et al. |
| 2007/0038184 A1 | 2/2007 | Bialecki et al. |
| 2007/0038185 A1 | 2/2007 | Albert et al. |
| 2007/0038188 A1 | 2/2007 | Bialecki et al. |
| 2007/0073221 A1 | 3/2007 | Bialecki et al. |
| 2007/0073222 A1 | 3/2007 | Lilley, Jr. et al. |
| 2007/0129689 A1 | 6/2007 | Woehr et al. |
| 2007/0156093 A1 | 7/2007 | Woehr |
| 2007/0161950 A1 | 7/2007 | Carlyon et al. |
| 2007/0179447 A1 | 8/2007 | Carrez et al. |

* cited by examiner

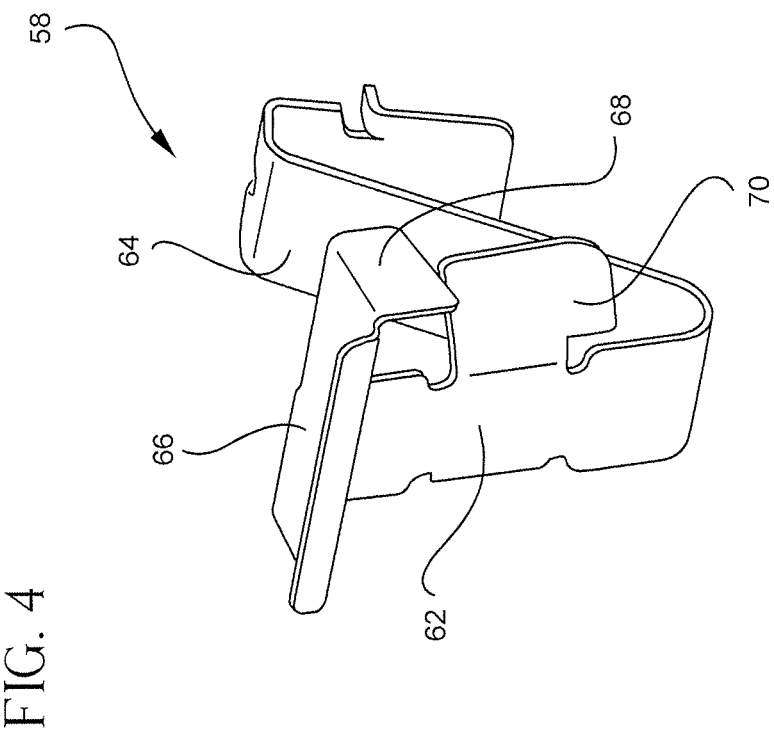
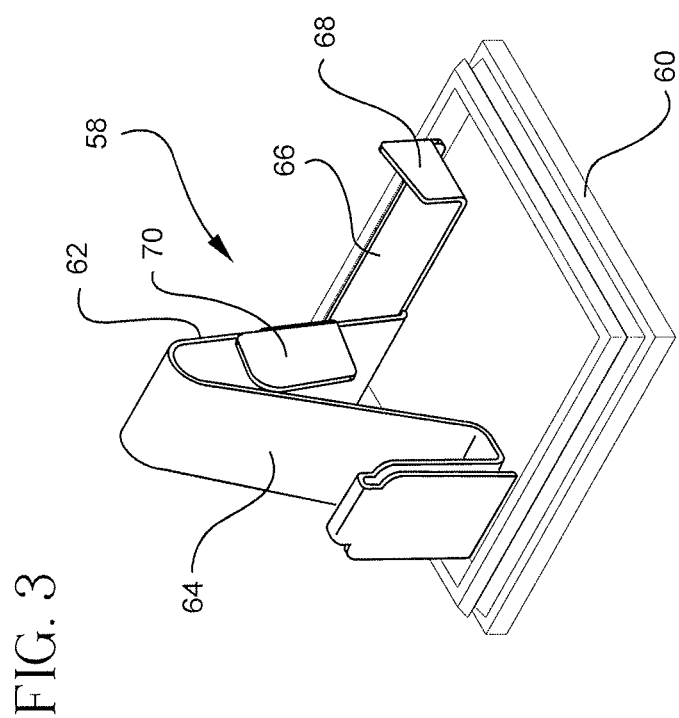
FIG. 3
FIG. 4

NEEDLE SHIELDING FLAG STRUCTURES

RELATED APPLICATIONS

This application claims the benefit of U.S. Provisional Application No. 60/867,047, filed Nov. 22, 2006, entitled NEEDLE SHIELD, which is incorporated herein by reference.

BACKGROUND OF THE INVENTION

This invention relates generally to vascular access devices and methods, including needle shield assemblies and devices used with catheter assemblies. Generally, vascular access devices are used for communicating fluid with the vascular system of patients. For example, catheters are used for infusing fluid, such as normal saline solution, various medicaments, and total parenteral nutrition, into a patient, withdrawing blood from a patient, or monitoring various parameters of the patient's vascular system.

A common type of intravenous (IV) catheter is an over-the-needle peripheral IV catheter. As its name implies, an over-the-needle catheter is mounted over an introducer needle having a sharp distal tip. At least the inner surface of the distal portion of the catheter tightly engages the outer surface of the needle to prevent peelback of the catheter and thus facilitate insertion of the catheter into the blood vessel. The catheter and the introducer needle are assembled so that the distal tip of the introducer needle extends beyond the distal tip of the catheter with the bevel of the needle facing up away from the patient's skin. The catheter and introducer needle are generally inserted at a shallow angle through the patient's skin into a blood vessel.

In order to verify proper placement of the needle and/or catheter in the blood vessel, the clinician generally confirms that there is "flashback" of blood in a flashback chamber of the catheter assembly. Once proper placement of the catheter into the blood vessel is confirmed, the clinician may apply pressure to the blood vessel by pressing down on the patient's skin over the blood vessel distal of the introducer needle and the catheter. This finger pressure occludes the vessel, minimizing further blood flow through the introducer needle and the catheter.

The clinician may then withdraw the introducer needle from the catheter. The introducer needle may be withdrawn into a needle tip shield device that covers the needle tip and prevents accidental needle sticks. In general, a needle shield includes a housing, a sleeve, or other similar device that is designed such that when the needle is withdrawn from the patient, the needle tip will be trapped/captured within the needle tip shield. The purpose of these needle tip shield devices is to house the tip of the needle in a secure location, thereby avoiding the possibility of needle sticks after the needle and needle shield device are separated from the catheter, which is left in place to provide intravenous access to the patient.

Various systems and methods are needed to provide needle tip shields that provide protection from the tip of a needle after needle use.

BRIEF SUMMARY OF THE INVENTION

The present invention has been developed in response to problems and needs in the art that have not yet been fully resolved by currently available vascular access systems and methods. Thus, these systems and methods are developed to provide more efficient vascular access systems and methods capable of ensuring proper needle tip protection.

An extravascular system for accessing the vasculature of a patient may include a catheter, a needle disposed within the catheter, and/or a needle tip shield assembly. The needle tip shield assembly may have a needle cap, the needle cap may have a needle shield, and the needle shield may have one or more flags. In one embodiment, the flags may include a first flag and a second flag. The first flag and the second flag may form an engageable barrier through which the needle cannot penetrate once the barrier is engaged. The needle shield may be a V-clip.

The V-clip may include a first arm and a second arm, and the first flag may be secured to the first arm while the second flag may be secured to the second arm. The first arm may come into proximity with the second arm as the V-clip compresses. The first arm and the second arm may extend away from each other as the barrier engages. The V-clip may expand after the needle is withdrawn from a surface adjacent the V-clip first arm. The first flag and the second flag may form a barrier between the first arm and the second arm after the V-clip is expanded.

The multiple flags may be transverse barriers. Either the first and/or the second flag may be located in the middle, front, and/or back of the first and/or second arms. The first flag and the second flag may provide structural support for each other. The first flag may be spaced apart from the second flag so as to avoid any collision between the first flag and the second flag.

The flags may receive structural reinforcement by the formation of one or more dents in the flag bend. The flag may include a single dent and it may include multiple dents. The dents may be located at any desired location along the flag bend.

A method for manufacturing an extravascular system for accessing the vasculature of a patient may include providing a catheter, providing a needle, disposing the needle within the catheter, providing a needle tip shield assembly having a needle cap, and/or disposing the needle within the needle tip assembly. The needle cap may have a needle shield, and the needle shield may have multiple flags. The method may also include forming a first flag and a second flag on the needle shield, forming an engageable barrier through which the needle cannot penetrate once the barrier is engaged, and/or forming the needle shield as a V-clip.

The method may also include forming a first arm and a second arm within the V-clip, and forming the first flag on the first arm and the second flag on the second arm. The method may also include placing the first arm into proximity with the second arm while compressing the V-clip. The method may also include expanding the V-clip, engaging the barrier, and/or extending the first arm away from the second arm. The method may also include expanding the V-clip while withdrawing the needle from a surface adjacent the V-clip first arm and/or forming a barrier with the first flag and the second flag between the first arm and the second arm after expanding the V-clip.

The method may also include forming multiple flags as transverse barriers. The method may also include forming the first and/or second flag in the middle, front, and/or back of the first and/or second arms. The method may also include orienting the first flag and the second flag to provide structural support for each other, especially in the situation where the needle is moved into a position of attempted re-penetration. In that situation the flags provide structural support for each other in order to counter the force of the needle moving forward toward re-penetration. The method may also include separating the first flag from the second flag so as to avoid any collision between the first flag and the second flag.

An extravascular system for accessing the vasculature of a patient may include a catheter, a needle disposed within the catheter, and/or a needle tip shield assembly. The needle tip shield assembly may have a needle cap. The needle may be disposed within the needle cap. The needle cap may have a needle shield. The needle shield may have barrier means for shielding the needle from re-penetrating the needle cap.

These and other features and advantages of the present invention may be incorporated into certain embodiments of the invention and will become more fully apparent from the following description and appended claims, or may be learned by the practice of the invention as set forth hereinafter. The present invention does not require that all the advantageous features and all the advantages described herein be incorporated into every embodiment of the invention.

BRIEF DESCRIPTION OF THE SEVERAL VIEWS OF THE DRAWINGS

In order that the manner in which the above-recited and other features and advantages of the invention are obtained will be readily understood, a more particular description of the invention briefly described above will be rendered by reference to specific embodiments thereof which are illustrated in the appended drawings. These drawings depict only typical embodiments of the invention and are not therefore to be considered to limit the scope of the invention.

FIG. 3 is a perspective view of a V-clip and housing cover within the environment of a needle cap.

FIG. 4 is a perspective view of a V-clip.

DETAILED DESCRIPTION OF THE INVENTION

The presently preferred embodiments of the present invention will be best understood by reference to the drawings, wherein like reference numbers indicate identical or functionally similar elements. It will be readily understood that the components of the present invention, as generally described and illustrated in the figures herein, could be arranged and designed in a wide variety of different configurations. Thus, the following more detailed description, as represented in the figures, is not intended to limit the scope of the invention as claimed, but is merely representative of presently preferred embodiments of the invention.

Figure 1:
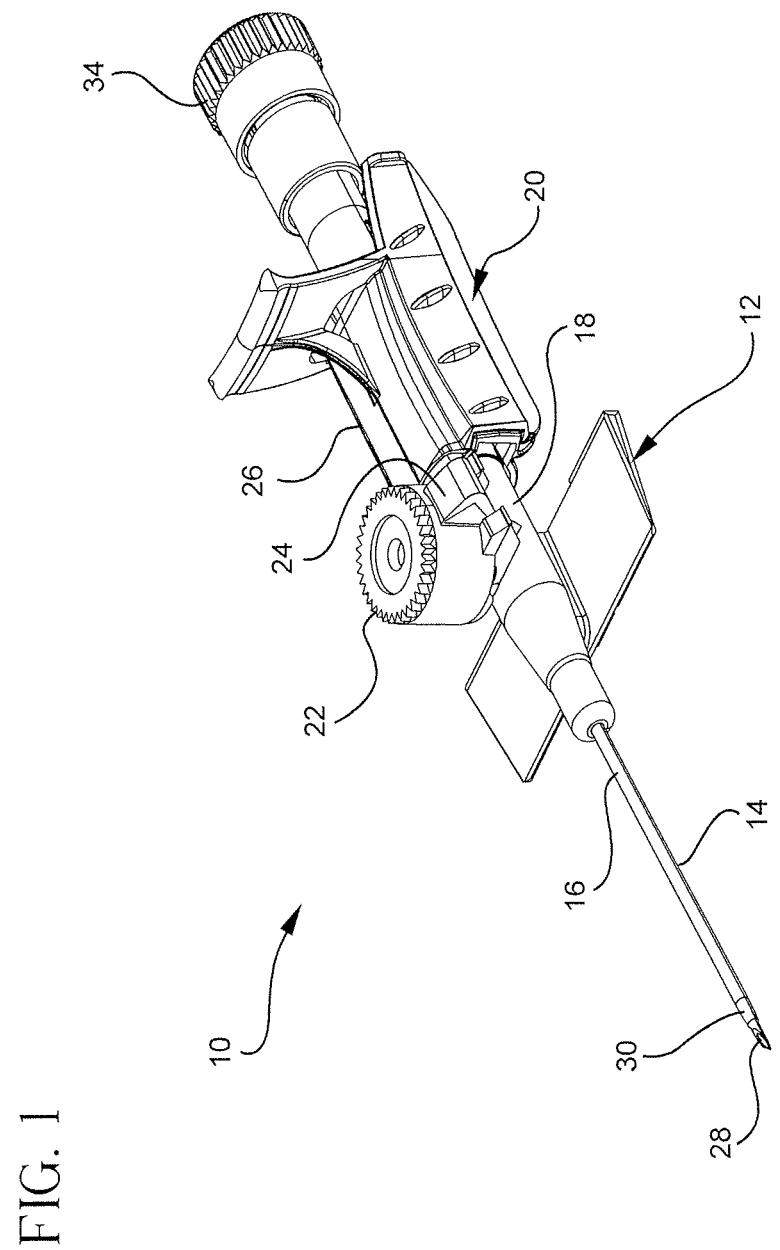
FIG. 1 is a perspective view of a catheter assembly.

Referring to FIG. 1, a perspective view illustrates an example of an extravascular system 10 of multiple vascular access devices. In this example the extravascular system 10 includes a catheter assembly 12 and a needle assembly 20. The catheter assembly 12 includes a vascular access device, such as a catheter 14, having an insertion portion 16 and an access portion 18. The access portion 18 includes a positioning groove (not shown) for use in securing the catheter 14 in place prior to placement and release. Also illustrated in FIG. 1 is a protection cap 22 positioned above the catheter assembly 12. The protection cap 22 may cover an access port which provides access into the catheter 14.

As mentioned above, FIG. 1 also illustrates a needle assembly 20. The needle assembly includes a needle cap 24 and a needle hub 26. The needle hub 26 is configured such that it will contain the needle tip 28 when the needle 30 is removed from the catheter 14. The needle hub 26 is securely attached to the needle 30 and provides for manipulation of the needle 30 and placement of the catheter 14 within the vasculature of a patient. The needle hub 26 may include grips 32 which allow for more secure gripping of the needle hub 26 and maneuvering of the needle 30. In addition, the needle hub 26 may include a plug 34 which is attached to the end of the device.

Figure 2:
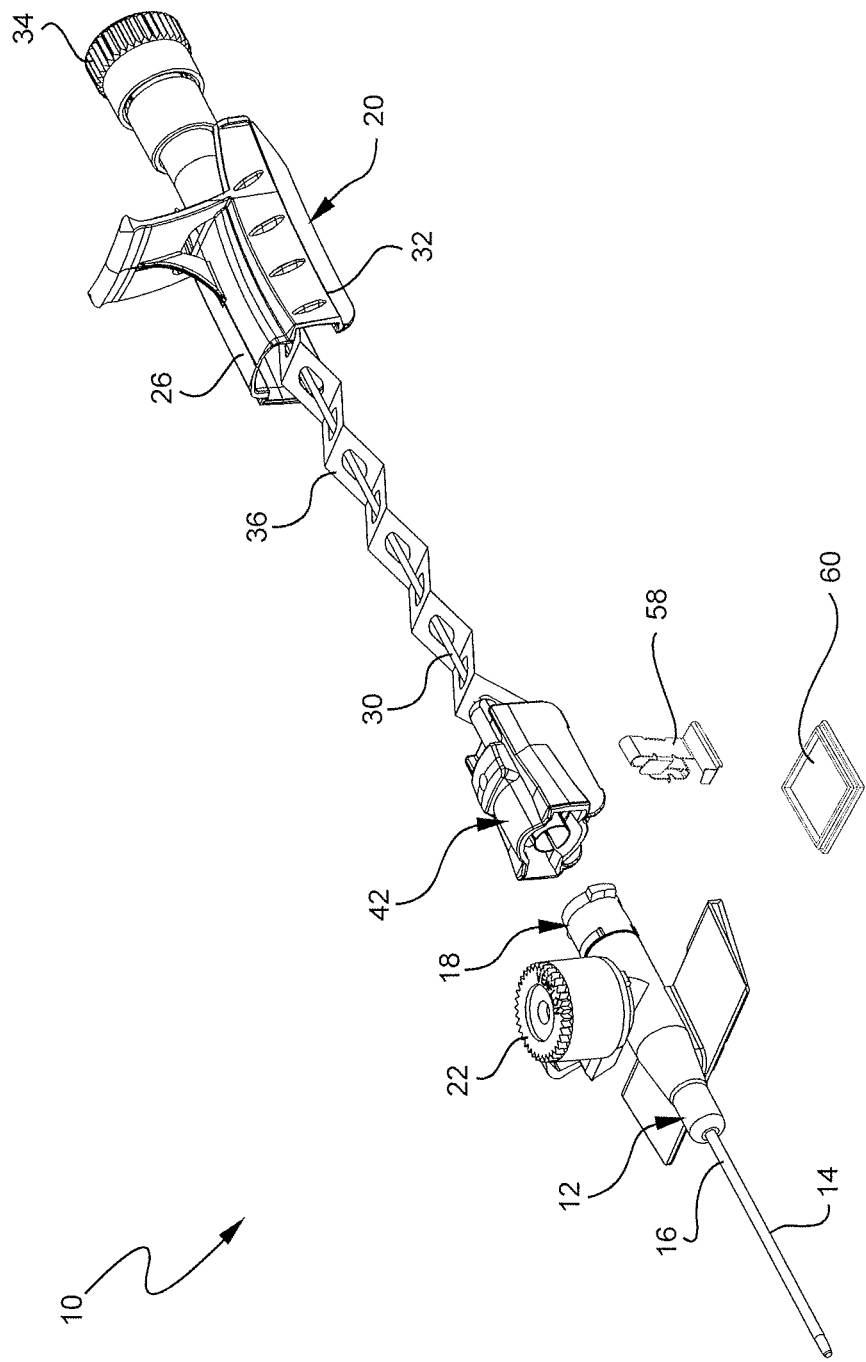
FIG. 2 is an exploded view of the catheter assembly of FIG. 1.

Referring now to FIG. 2, the extravascular system 10 is illustrated in an exploded view. As with FIG. 1, the catheter assembly 12 and needle assembly 20 are shown. As discussed above, the catheter assembly includes a catheter 14 for placement within the vascular system of a patient. The catheter assembly includes the insertion portion 16 of the catheter 14 and an access portion 18 of the catheter 14. The access portion 18 is configured such that the catheter 14 can be attached to further medical devices or tubing, such as for the administration of fluids to the patient. In that regard, the illustrated catheter assembly 12 also includes a protection cap 22 which covers an access port which provides further access to the catheter 14.

Also illustrated in FIG. 2 is the needle hub 26 in a position in which the needle 30 has been fully retracted from the catheter 14. As mentioned above, the needle hub 26 as illustrated includes grips 32 for use in retracting and manipulating the position of the needle 30. The needle hub 26 is also closed at its proximal end by the plug 34.

Extending between the needle cap 24 and the needle hub 26 is a tether 36. The length of the tether 38 is selected such that when the needle hub 26 is retracted and the needle 30 is removed from the catheter, that the needle tip 28 of needle 30 is securely housed within the needle cap 24. The tether 36 may be folded in an accordion configuration, may be straight, or take any other desired configuration.

As illustrated in FIG. 2, the needle tip 28 is secured within the needle cap 24. The tether 36 is in the extended position between the needle cap 24 and the needle hub 26. Thus, the needle 30 is prevented from being pulled out of the needle cap 24. The interior of the needle cap 24 also cooperates with structures on the needle (not shown) and the shield 58 to prevent the needle from moving forward out of the needle cap 24. The shield 58 is also illustrated in FIG. 2, as is the clip housing cover 60, both of which are described in further detail below.

Referring to FIG. 3, the V-shaped clip shield 58 and V-clip housing cover 60 are shown within the environment of a needle cap 24 in perspective view. The shield 58 is a V-clip having a first arm 62 and a second arm 64. The first arm 62 includes an extension 66 forming a pawl 68 at the end of the extension 66. The first arm 62 and/or the second arm 64 may also include a needle tip shield flag 70 capable of halting the advancement of the needle tip 44 after the V-clip 58 is engaged. The shield flag 70 is used to prevent the reemergence of the sharp needle tip 44 from the needle cap 24 after the needle 30 has been shielded by the cap 24.

Prior to activation of the extravascular system 10, the arms 62, 64 are held in close proximity by the needle 30. In this position the pawl locks the catheter assembly 12 to the needle assembly 20. When the needle 30 is retracted, the V-clip is released such that the arms 62, 64 return to the position generally illustrated in FIG. 3. In this position, the catheter assembly 12 is released from the needle assembly 20 such that the two can be separated as illustrated in FIG. 2. At the same time, as will be discussed in further detail below, the shield flag, or flags, 70, 72 are positioned such that they block re-penetration by the needle tip 28.

Referring to FIG. 4, an example of a shield 58 for use with a needle cap 24 within an extravascular system is shown in perspective view. The shield 58 is a V-clip having a first arm 62 and a second arm 64. The first arm 62 includes an extension 66 forming a pawl 68 at the end of the extension 66. The first arm 62 and/or the second arm 64 may also include a needle tip shield flag 70 capable of halting the advancement of the needle tip 44 after the V-clip 58 is engaged. The shield flag 70 is used to prevent the reemergence of the sharp needle tip 44 from the needle cap 24 after the needle 30 has been shielded by the cap 24. The shield flag 70 may also be called a shield, a flag, a flap, and/or a barrier.

Figure 5:
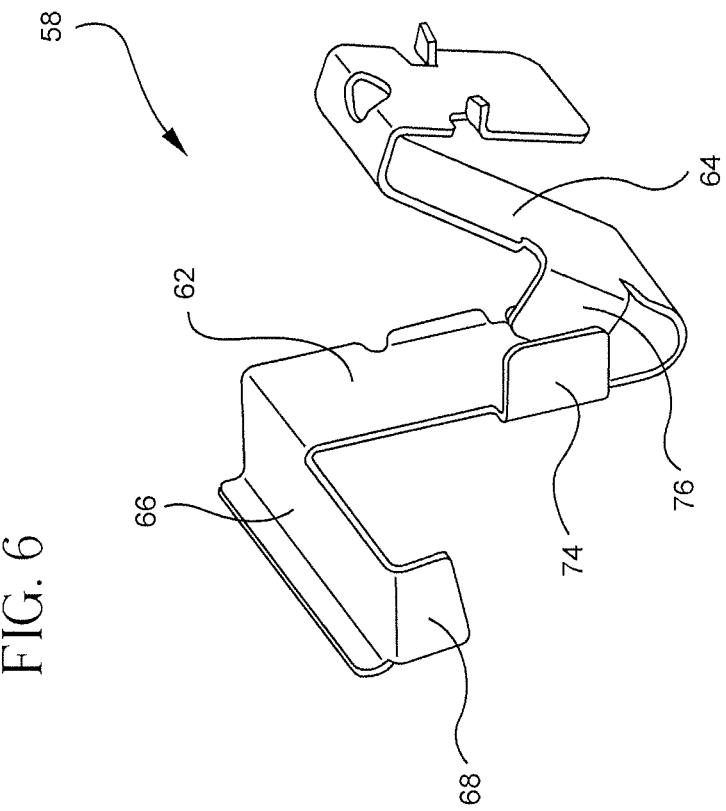
FIG. 5 is a perspective view of a V-clip having two flags.

Referring to FIG. 5, a shield 58 for use with a needle cap 24 within an extravascular system is shown in perspective view. The shield 58 is a V-clip having a first arm 62 and a second arm 64. The first arm 62 includes an extension 66 forming a pawl 68 at the end of the extension 66. The first arm 62 includes the flag 70 shown and described with reference to FIG. 4. The second arm 64 includes an additional flag 72. The additional flag 72 overlaps with the first flag 70 to provide an additional barrier or shield through which the needle 40 is prevented from passing, thus preventing penetration of the V-clip 58. The second flag 72 is located within the center of the width of the second arm 64, and has been punched through the sheet metal and bent out from the center portion of the second arm 64. The size, shape and/or location of either of the flags 70 and/or 72 may be modified in order to provide the shielding needed to prevent re-penetration of a needle tip 44 once a needle 40 has been retracted into the needle cap 24 and the V-clip 58 has been engaged.

Ensuring that the needle tip 28 of a needle 30 does not re-penetrate once it has engaged the V-clip 58 of a needle cap 24 will provide a catheter assembly 10 of maximum safety for operators and/or clinicians. Since the design parameters for various needle caps 24 change from one extravascular system to the next, a variety of flag configurations as shown, for example, above in FIG. 5 may be preferable to ensure that the needle tip 28 does not re-penetrate after entry into the needle cap 24. For example, in certain IV catheters, a V-clip flag having large dimensions may not fully cover the path through which a needle 30 would travel to re-penetrate the needle cap 24. Further, large dimension needles may form a slightly different trajectory as the tip of the bevel of the large needle 30 extends past a flag intended to catch the needle tip 28. In addition, various needles 30 may become bent during use, and the play between bent or straight needles 30 and their surrounding environment may enable the needle to take trajectories that avoid the flag which is intended to prevent re-penetration of the needle tips 28. Thus, maximum protection and/or coverage of the path through which a needle tip 28 may travel between the arms 62 and 64 of a V-clip 58 is preferred.

When the needle 30 is fully extended within a catheter assembly 10 and the V-clip 58 is compressed prior to engagement, a surface of the needle 30 is in direct contact with the first arm 62. After the needle 30 is withdrawn such that the tip 28 of the needle 30 is pulled beyond the arm 62, the V-clip 58 will spring open from its compressed position. In its open position, the first arm 62 is extended away from the second arm 64 and at least a portion of the flags 70 and 72 overlaps with at least a portion of the flags 70 and 72. In its compressed position, the first arm 62 is close to and potentially parallel with the second arm 64, and the flags 70 and 72 substantially overlap. The length and/or width of the flags 70 and 72 may cause a surface of the flags 70 and 72 to be in contact with the opposing respective arm 62 and/or 64. Since the V-clip 58 can only accommodate a flag of a certain width as a result of the distance between the parallel arms 62 and 64 in the V-clip's 58 compressed state, multiple flags are desirable in order to provide an increased surface area for protecting the tip 28 of a needle 30 from re-penetrating the needle cap 24. Thus, since the design constraints of the V-clip 58 preclude a flag that is much larger than the flag 70, the additional flag 72 or any other additional flag will provide the needed surface area coverage between the first arm 62 and the second arm 64. The location of any additional flag, as previously mentioned, may be modified as desired depending on the specific product configuration and use. The flags will cooperate with each other in order to close all possibilities for a needle tip 44 to come outside any of the flags.

Figure 6:
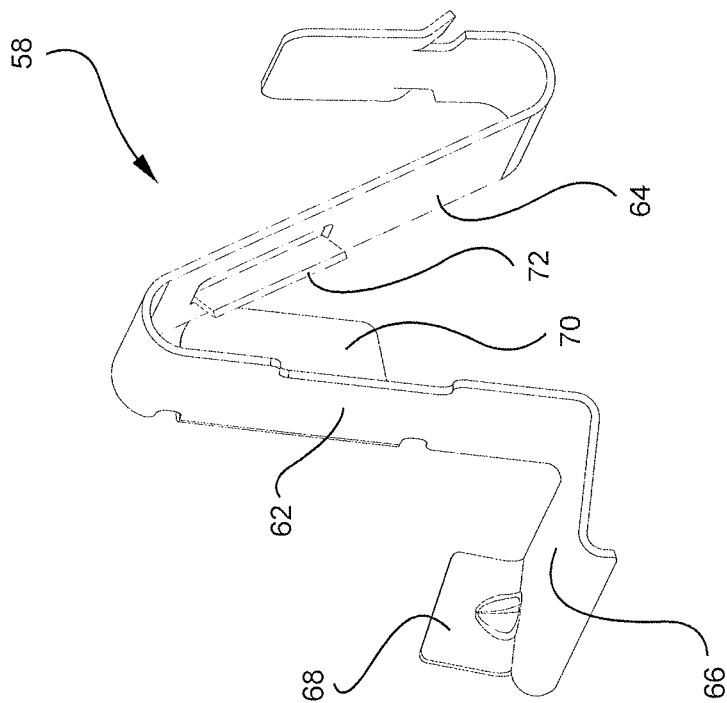
FIG. 6 is a perspective view of a V-clip having two flags.

Referring to FIG. 6, a first flag 74 may be located on the front end of a first arm 62 and a second flag 76 may be located on the front end of a second arm 64 of a V-clip 58. The first flag 74 and second flag 76 are in close and/or direct proximity such that the two flags will provide structural support for each other as the tip 28 of a needle 40 is pressed against one of the flags 74 and/or 76. However, because of the close proximity of the flags 74 and 76, the manufacture of the V-clip 58 may become difficult. For example, the flags 74 and 76 may catch against each other, inhibiting the movement of the first arm 62 towards the second arm 64. In order to avoid the close proximity and catching of flag surfaces against each other, an alternate embodiment, such as the embodiment described with reference to FIG. 5 and/or the embodiment described with reference to the following FIG. 7, may be preferred.

Figure 7:
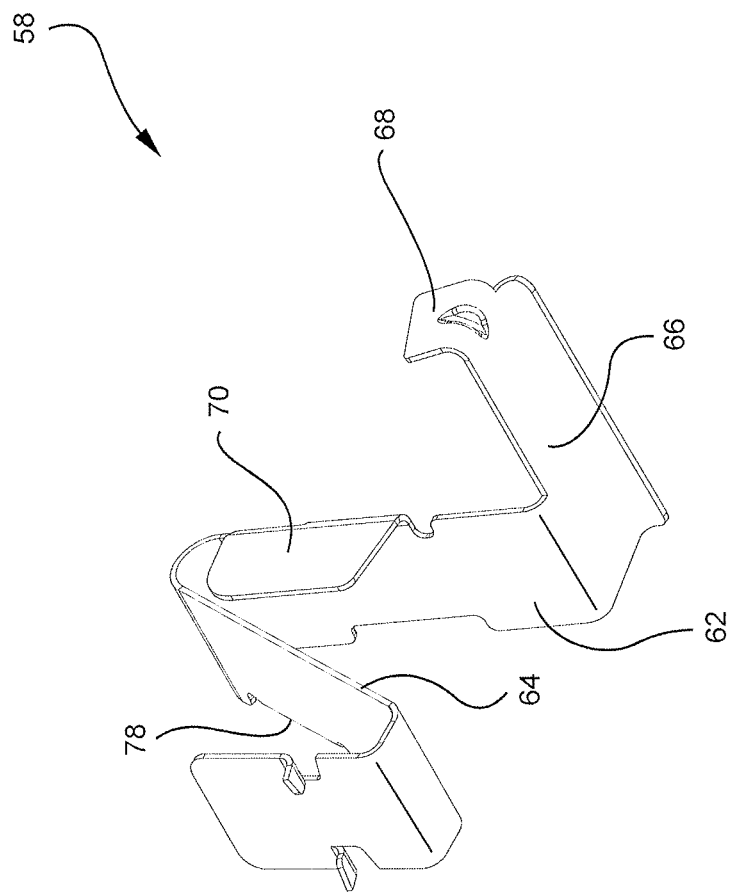
FIG. 7 is a perspective view of a V-clip having two flags

Referring to FIG. 7, a first flag 70, such as the first flag 70 described with reference to FIG. 5, is provided on a first arm 62 and a second flag 78 is provided on the back end of a second arm 64 of a V-clip 58. Since the first flag 70 is formed on the front end of the first arm 62 and the second flag 78 is formed on the back end of the second arm 64, the flags 70 and 78 will not provide structural support for each other. However, because the first flag 70 is distant from the second flag 78, the surfaces of the two flags 70 and 78 will not catch onto, intersect with, and/or collide with each other, inhibiting the movement of the first arm 62 towards the second arm 64.

Thus, the embodiments herein describe various transverse barriers and/or flags capable of shielding the tip 28 of a needle 30 from re-emerging or re-penetrating out of the needle cap 24 of a catheter assembly 10 after the needle tip has entered into the needle cap 24. Although the embodiments shown herein include only two flags, any number of flags may be used in any orientation, shape, size, and/or location in communication with a V-clip and/or other shield for an extravascular system such as a catheter assembly.

Figure 8:
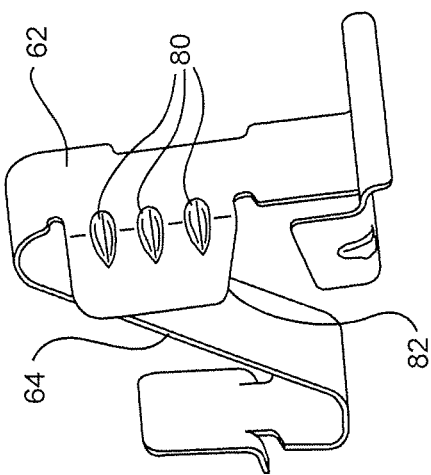
FIG. 8 is a perspective view of a V-clip having two flags and a dent in the flag bend.
Figure 9:
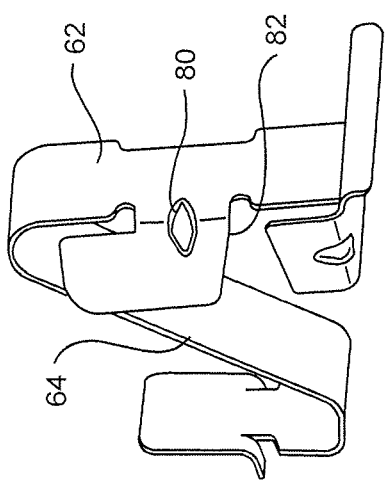
FIG. 9 is a perspective view of a V-clip having two flags and a plurality of dents in the flag bend.

Reference is now made to FIGS. 8 and 9. These Figures include a V-clip 58 having a first arm 62 and a second arm 64. The V-clip also includes a flag 70 extending from arm 62 in a similar manner as that described with reference to FIG. 4. In the embodiment illustrated in FIG. 8, however, a dent 80 is formed in the flag bend 82 between the flag 70 and arm 62. It is found that forming such a dent 80 in the flag bend 82 increases the structural strength of the flag 70. FIG. 9 illustrates a similar V-clip 58 having multiple dents along the flag bend 82. The number and positions of the plurality of dents is not limited. They can be placed at any desired location along the bend 82.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

The invention claimed is:

1. An extravascular system for accessing the vasculature of a patient, comprising:
   a catheter assembly including a catheter;
   a needle disposed within the catheter; and
   a needle tip shield assembly having a needle cap; and
   a needle shield housed within the needle cap during and after removal of the needle from the catheter assembly, the needle shield comprising a first arm, a second arm, a first flag, and a second flag, the first flag and second flags configured to prevent re-penetration of the needle when the needle is removed from the catheter;
   wherein, when the needle is within the catheter, the needle shield is in a compressed position with the first arm and second arm held in close proximity such that only the first arm directly contacts a surface of the needle and such that the first arm is interposed between the needle and the second arm;
   wherein, when the needle is removed from the catheter, the needle shield opens from the compressed position such that the first flag and the second flag form an engageable barrier through which the needle cannot penetrate once the barrier is engaged.

2. The system of claim 1, wherein the first arm and the second arm are connected such that the arms form a V-clip.

3. The system of claim 1 further comprising a bend between the flag and the needle shield and further comprising at least one dent on the bend.

4. The system of claim 3 further comprising a plurality of dents on the bend.

5. The system of claim 2, wherein the first flag is secured to the first arm and the second flag is secured to the second arm.

6. The system of claim 5, wherein the first arm comes into proximity with the second arm as the V-clip compresses.

7. The system of claim 6, wherein the first arm and the second arm extend away from each other as the V-clip expands and the barrier engages.

8. The system of claim 7, wherein the V-clip expands after the needle is withdrawn from a surface adjacent the V-clip first arm.

9. The system of claim 8, wherein the first flag and the second flag form a barrier between the first arm and the second arm after the V-clip is expanded.

10. The system of claim 9, wherein the first flag and the second flag provide structural support for each other.

11. The system of claim 9, wherein the first flag is spaced apart from the second flag so as to avoid any collision between the first flag and the second flag.

12. The system of claim 1 where the needle shield comprises an extension having a pawl.

13. An extravascular system for accessing the vasculature of a patient, comprising:
    a catheter assembly including a catheter;
    a needle disposed within the catheter;
    a needle tip shield assembly having a needle cap, the needle disposed within the needle cap; and
    a needle shield housed within the needle cap during and after removal of the needle from the catheter assembly, the needle shield comprising a first arm, a second arm and barriers for shielding the needle from re-penetrating the needle cap;
    wherein, when the needle is within the catheter, the needle shield is in a compressed position with the first arm and second arm held in close proximity such that only the first arm directly contacts a surface of the needle and such that the first arm is interposed between the needle and the second arm;
    wherein when the needle is removed from the catheter, the needle shield opens from the compressed position such that the barriers engage to prevent re-penetration of the needle.

14. The extravascular system of claim 13 wherein said barrier comprises one or more flags.

15. The extravascular system of claim 13 wherein the needle shield comprises an extension having a pawl.

16. An extravascular system for accessing the vasculature of a patient, comprising:
    a catheter assembly;
    a needle cap that selectively couples to the catheter assembly;
    a needle selectively inserted through the catheter assembly and the needle cap;
    a compressible shield comprising a first arm and a second arm, the compressible shield disposed within the needle cap in a compressed state when a needle is inserted through the needle cap, the compressible shield being in an open state when the needle is withdrawn from the catheter assembly into the needle cap; and
    a first flag and a second flag coupled to the compressible shield and forming an engageable barrier to shield the needle from re-penetration of the needle cap when the compressible shield is in an open state;
    wherein, when the compressible shield is in a compressed position, the first arm and second arm are held in close proximity such that only the first arm directly contacts a surface of the needle and such that the first arm is interposed between the needle and the second arm.

17. The extravascular system of claim 16, further comprising:
    a hole in the distal end of the needle cap, wherein the needle is selectively inserted through the hole; and
    wherein the flag coupled to the compressible shield covers the entry hole when the compressible shield is in the open state.

18. The extravascular system of claim 16, wherein compressible shield is housed within an inner cavity of the needle cap, and wherein the needle is selectively inserted through the inner cavity of the needle cap.

* * * * *